United States Patent [19]

Husain et al.

[11] Patent Number: 5,093,029
[45] Date of Patent: Mar. 3, 1992

[54] BREAKING EMULSIONS OF ALKANESULFONYL CHLORIDES IN AQUEOUS HYDROCHLORIC ACID

[75] Inventors: Altaf Husain, East Norriton; Michael D. Mayo, Philadelphia; Pamela J. Peerce-Landers, Lower Pottsgrove Township, Montgomery County, all of Pa.

[73] Assignee: Atochem North America, Inc., Philadelphia, Pa.

[21] Appl. No.: 392,677

[22] Filed: Aug. 11, 1989

[51] Int. Cl.$^5$ .................. B01D 17/022; B01D 17/04
[52] U.S. Cl. ........................... 252/324; 210/694; 210/708; 252/320
[58] Field of Search ............ 252/320, 324; 210/708, 210/694; 568/28

[56] References Cited

U.S. PATENT DOCUMENTS

| | | | |
|---|---|---|---|
| 2,336,482 | 12/1943 | Hatfield | 252/324 X |
| 2,464,204 | 3/1949 | Baker | 252/324 X |
| 2,665,305 | 1/1954 | Cier | 562/33 |
| 3,268,456 | 8/1966 | Fruth | 252/324 X |
| 3,860,531 | 1/1974 | Cole et al. | 502/167 |
| 3,919,081 | 11/1975 | Mail | 252/331 X |
| 4,550,105 | 10/1985 | Matsuo et al. | 544/331 X |
| 4,699,736 | 10/1987 | Gongora et al. | 562/829 |

FOREIGN PATENT DOCUMENTS 2310749  3/1973  Fed. Rep. of Germany .
2536807  12/1976  Fed. Rep. of Germany .

OTHER PUBLICATIONS

Langdon and Wasan, *Recent Developments in Separation Science* (1979); pp. 159–183.
K. J. Lissant, "Emulsions and Emulsion Technology", Marcel, Dekker, Inc., New York (1974); pp. 52, 53, 118 & 119.
"Coalescence. Aspects Industriels", *Revue de l'Institute Francais du Petrole*, XXVII, No. 5, pp. 763–783 (Sep.–Oct. 1972).

*Primary Examiner*—Richard D. Lovering
*Attorney, Agent, or Firm*—Panitch Schwarze Jacobs & Nadel

[57] ABSTRACT

A process for separating emulsions of alkanesulfonyl chloride in aqueous hydrochloric acid comprises passing the emulsion through a carbon bed, a graphite bed, a layer of alkanesulfonyl chloride or a combination thereof; and allowing the emulsion to enter a settling vessel.

6 Claims, No Drawings

5,093,029

BREAKING EMULSIONS OF ALKANESULFONYL CHLORIDES IN AQUEOUS HYDROCHLORIC ACID

FIELD OF THE INVENTION

The present invention relates to a process for separating emulsions of alkanesulfonyl chloride in aqueous hydrochloric acid.

BACKGROUND OF THE INVENTION

It is known in the art that fine emulsions, which are dispersions of one immiscible liquid in another, can be produced by vigorous agitation of the combination of the two liquids. An emulsion is a dispersed system containing at least two immiscible liquid phases. Generally, there are three components to an emulsion, a dispersed phase, a continuous phase (i.e., the dispersion medium) and an emulsifying agent.

The production of such emulsions is important in certain industrial applications, e.g., liquid-liquid extraction operations, where it is necessary to create the highest possible contact area between the two liquids in order to obtain high extraction efficiencies. Such vigorous agitation techniques can produce extremely fine emulsions when the two liquids have similar densities.

Various processes have been used for separating the liquids forming the emulsions from the emulsions, as when the extraction or synthesis operation involving the emulsions is complete. For example, it is known in the art to use decanters for easy, gravity separations. For more difficult separations in which the droplets of the dispersed phase are small, it is necessary to increase the size of the dispersed phase droplets so that they can settle out of the continuous phase within a reasonable time. For this purpose, centrifugal coalescers, electrical coalescers and various bed-type coalescers are usually used. However, of these, only bed-type coalescers are capable of separating liquids with very similar densities.

In order to achieve this increased size of the dispersed droplets, various materials have been used to adsorb, on their surfaces, the dispersed liquid. This allows the smaller particles to more readily settle out of the continuous phase. Various theories have been advanced in order to explain the ability of different packing materials used in bed-type coalescers to promote strong coalescence between droplets of the dispersed phase in order to break fine emulsions. However, none of these theories is considered completely satisfactory.

For example, preferential wetting of the packing material by the dispersed phase is regarded as the controlling factor in some of the theories advanced. Packing materials are generally selected based upon their wettability by the dispersed phase. However, Gudeson in "Coalescence of Petroleum Compounds in Mixed Fibrous Beds", M. S. Thesis, Illinois Institute of Technology, (1965), reported that surface roughness of the packing material may be controlling, since coalescence occurs preferentially at certain fixed points of the packing material which are presumably the result of roughness.

Moreover, Bitten in "Study of Aviation-Fuel Filter/-Separators", Final Report No. IITRI-C6088-12, IIT Research Institute, p. 322, Chicago (May, 1969), obtained good separation of water from jet fuel by using Teflon® fibers which are phobic to both water and jet fuel. Microscopic examination of the Teflon® fibers demonstrated that the surfaces were, in fact, rough.

Various types of packing materials have been used in bed coalescers, including hydrophilic materials such as fiberglass, glass, ceramics, steel and synthetic polymers (e.g., polyurethanes). Various composite materials have been used for water in oil emulsions, while hydrophobic materials (principally, synthetic polymers, e.g., polypropylene) have been used for oil in water emulsions.

In U.S. Pat. No. 3,919,081, the use of acid-washed activated carbon particles was disclosed for separating hydrocarbons from waste water. Contrary to the conventional practice in the art which is to first contact the coalescing bed with the continuous phase in order to obtain maximum performance, this patent discloses that it is critical to presaturate the activated carbon bed with the hydrocarbons in order to obtain good coalescence.

"Coalescence. Industrial Aspects", *Revue de l'Institute Francais du Petrole*, XXVII, No. 5, pp. 763–783, (Sept.-Oct. 1972), discloses other methods which have been used to break liquid-liquid emulsions. However, these methods are highly specific for the particular emulsion system with which they are being used. Examples of some of the methods disclosed are refrigeration, heating, agitation, addition of an excess of the dispersed phase and violent agitation, addition of certain materials to chemically destroy or alter the emulsifying agent, addition of a solvent in which both phases are soluble and addition of powdered solids (e.g., graphite powder) to increase the efficiency of decanters for separating some oil in water emulsions.

Although it would appear that the addition of powdered carbon or graphite should be a general way of destabilizing oil in water emulsions, it has been found by the present inventors that the opposite is, in fact, true. Frequently, small graphite or carbon particles adsorb on the surface of the oil droplets, preventing their coalescence and thus stabilizing, rather than breaking the emulsion. Such emulsion stabilization due to the adsorption of finely divided foreign particles on the surface of the dispersed phase droplets is a common industrial problem and frequently the emulsion is pre-filtered in order to remove any such foreign particulates. Therefore, although carbon powder and graphite powder previously have been used to break oil in water emulsions, they are not widely used due to their tendency to produce fines which can stabilize the emulsions.

In the production of alkanesulfonyl chlorides by chloride oxidation of either the corresponding alkanethiol or dialkyl disulfide in aqueous hydrochloric acid, good mixing is necessary to maintain the poorly soluble starting materials and intermediate oxidation products dispersed in the reaction medium. Also, good mixing is important to prevent local excesses of chloride which can lead to side-chain chlorinated products. However, highly stable emulsions of the alkanesulfonyl chloride in the aqueous hydrochloric acid can result which are difficult to separate.

A reliable and effective process for separating highly stable emulsions of alkanesulfonyl chloride in aqueous hydrochloric acid is needed. The present invention provides an improved process to break such emulsions, which is accomplished by passing the emulsion through a coalescing bed of carbon or graphite, by passing the emulsion through a layer of alkanesulfonyl chloride, or by a combination thereof.

SUMMARY OF THE INVENTION

The present invention relates to a process for separating an emulsion of alkanesulfonyl chloride in aqueous hydrochloric acid comprising passing the emulsion through a carbon bed; and allowing the emulsion to enter a settling vessel.

In a further embodiment of the present invention, the emulsion separation may be achieved by passing an emulsion of alkanesulfonyl chloride in aqueous hydrochloric acid through a layer of alkanesulfonyl chloride. The emulsion is then allowed to enter a settling vessel.

DETAILED DESCRIPTION OF THE PREFERRED EMBODIMENTS

The process of the present invention comprises passing the emulsion of alkanesulfonyl chloride in aqueous hydrochloric acid emulsion first through a carbon bed to coalesce the small, suspended droplets of the alkanesulfonyl chloride. This has been found to facilitate gravity separation of the crude alkanesulfonyl chloride product from the aqueous hydrochloric acid reaction medium. The emulsion is then allowed to enter a settling vessel or decanter wherein separation is completed.

The types of alkanesulfonyl chloride solutions which may be treated with the present method are alkanesulfonyl chloride solutions wherein the alkane group comprises 1–5 carbon atoms.

Generally, any chemical form of carbon may be used in the carbon bed of the present method. However, it is preferred that the carbon be graphite.

To be effective in the separation process of the present invention, the carbon used in the separation bed must have physical characteristics which allow for separation or breaking the emulsion, rather than stabilizing the emulsion. The critical physical characteristics are primarily size and shape. The carbon particles used in the separation bed should be large enough not to be adsorbed on the surface of the drops of the dispersed phase of the emulsion to be separated. Thus, the carbon particles should be larger than the drops of the dispersed phase to be separated from the continuous phase. The shape of the carbon particles should be such that a significant breakage or powdering of the carbon does not result when the bed is formed or used. That is because powdered forms of carbon may cake up, resulting in reduced through-put. Moreover, the small particles of the powders may adsorb on the alkanesulfonyl chloride droplets, further impeding their coalescence and stabilizing the emulsion.

Generally, the appropriate physical form of the carbon or graphite to be used to form the coalescing bed in the present method is any form having the characteristics described above and should be dense enough to fall or pass through a saturated hydrochloric acid solution by gravity. Such physical forms of carbon include any of chips, pellets or felts, for example. Of these, carbon chips are presently preferred.

There are no specific requirements with regard to the carbon coalescing beds. That is, the height of the packing, the size of the carbon or graphite particles, etc., may be chosen as required by one skilled in the art dependent upon the flow rate through the bed, fineness of the emulsion, etc.

The design of the decanter or settling vessel employed in the method of the present invention is not critical, and any of the various designs known in the art may be used. For example, any of vertical decanters, horizontal decanters, inclined decanters, etc., may be used.

In a further embodiment of the present method, the emulsion breaking can be achieved by passing the emulsion through a layer of the alkanesulfonyl chloride to promote the coalescence of the alkanesulfonyl chloride droplets prior to allowing the stream to enter the decanter. The improved coalescence facilitates breaking of the emulsion.

There are no specific requirements as to the height of the alkanesulfonyl chloride layer, as long as it is effective in breaking the emulsion. The presently preferred layer of alkanesulfonyl chloride is at least about one inch high to about two inches high. The amount of the alkanesulfonyl chloride layer used may be chosen as required by one skilled in the art based upon the same or similar factors discussed above with regard to the carbon bed.

In the most preferred form of the present invention, the emulsion breaking is achieved by first passing the emulsion through a layer of the alkanesulfonyl chloride in order to promote coalescence of the dispersed alkanesulfonyl chloride droplets. The emulsion is then allowed to pass through a coalescing bed of carbon or graphite. Finally, the emulsion is allowed to enter a settling vessel, wherein separation is completed.

The process of the present invention will now be illustrated in more detail by reference to the following specific, non-limiting example.

EXAMPLE

The apparatus used in the following example consisted simply of an emulsifier, a circulating pump and a coalescer/decanter. For the coalescer/decanter, an unmodified, glass condenser coil was used. The condenser coil was a cylindrical glass vessel, approximately 70 mm in diameter and 460 mm high with a side-arm positioned about half way up the vessel, a three-way parallel Teflon ® stopcock at the bottom for take-off and an internal glass coil for circulating the heat transfer fluid.

Aqueous hydrochloric acid containing approximately 10 wt. % methanesulfonyl chloride was emulsified and pumped into the bottom of the coalescer/decanter through ¼ inch (outside diameter) tubing, fed in from the top at a rate of 260 ml/min. As indicated in the following Table, initially, no packing (Run O) was used in the coalescer/decanter, and then, various different packings (Runs 1–8) were was placed in the bottom of the coalescer/decanter. The liquid from the coalescer/decanter was recirculated back to the emulsifier through the glass side arm. The maximum residence time in the coalescer/decanter was only about 5–7 seconds and the emulsion breaking was obtained using the process of the invention as described below.

1425 g of concentrated (37 wt. %) reagent grade aqueous hydrochloric acid containing approximately 10 wt. % methanesulfonyl chloride was charged to the system and emulsified, producing a milky white liquid phase.

The efficacy of the specific separation methods tested was measured by the appearance of the emulsion in the coalescer/decanter and by the wt. % of the methanesulfonyl chloride in the aqueous hydrochloric acid returning to the emulsifier as determined by gas chromatography. The results are tabulated below.

TABLE

| Run # | Temp.[1] (°C.) | HCl Conc. (wt. %) | Packing | Additive | MSC Found[2] (wt. %) | Comments |
|---|---|---|---|---|---|---|
| 0 | 8-10 | 37 | None | None | 9.53 | Original System Charge - milky white emulsion |
| 1 | 8-10 | 37 | ca. 1" layer of MSC (100 ml) | None | 9.75 | Turbidity reduced somewhat compared to Run No. 0. Individual MSC droplets, ca. 0.5-1 mm in diameter observed. |
| 2 | 8-10 | 37 | ca. ½" layer of Teflon ® chips on top of 1" MSC layer | None | 9.81 9.74 | No change in turbidity from Run #1. |
| 3 | 8-10 | 37 | Same as Run #2 plus additional ca. 1" MSC layer | None | 9.47 | No change in turbidity from Run #1. |
| 4 | 8-10 | 37 | Same as Run #3 plus ca. ¾" layer of glass beads on top of Teflon ® chips | None | 9.57 | No change in turbidity from Run #1. |
| 5 | 8-10 | 31 | Same as Run #4 | Water (270 ml) | 7.47 | No change in turbidity from Run #1. Simple dilution to reduce MSC level to 8.05 wt. %. |
| 6 | 8-10 | 31 | Same as Run #4 | LiCl to yield 2.9 wt. % in the HCl | 6.67 | No change in turbidity from Run #1. |
| 7 | 17 | 31 | Same as Run #4 | Same as Run #6 | 6.59 | Somewhat less turbid than Run #6. |
| 8 | 17 | 31 | Same as Run #4 plus ca. ¾" layer of Calgon CPG carbon chips on top of glass beads | Same as Run #6 | 5.81 | Liquid is clearer than in Run #7. Can see droplets of MSC, which are much larger than without carbon chips, settling out. |

[1]Temperature in the coalescer/decanter.
[2]MSC = methane sulfonyl chloride. Wt. % MSC found in the liquid being circulated back to the emulsifier through the glass side arm.

In the Table, the less methanasulfonyl chloride returning to the emulsifier (i.e., the less MSC found), the better a particular method performed in breaking the emulsion and promoting settling of methanesulfonic acid. These determinations must be considered along with the turbidity determinations. A lower turbidity demonstrates a better breaking of the emulsion.

The data set forth in the Table demonstrates that the carbon bed and the layer of methanesulfonyl chloride of Run No. 8 were entirely effective in breaking the methanesulfonyl chloride/aqueous hydrochloric acid emulsion under the conditions employed. Since the other conditions of Run No. 8 were identical to Run No. 7, except the addition of the carbon chips, the carbon chips must have been responsible for the effective breaking of the emulsion.

Moreover, it can been seen with respect to Run No. 1 that by passing the emulsion through a layer of methanesulfonyl chloride (MSC), the size of the MSC droplets was increased to approximately 0.5 to 1.0 mm in diameter. Although the amount of methanesulfonyl chloride returning to the vessel in the recirculating liquid did not decrease as sharply as other runs, the turbidity of the emulsion was reduced and size of the methanesulfonyl chloride droplets increased significantly, which would aid one attempting to break such an emulsion.

In contrast, as evidenced by the lack of change in the turbidity of the liquid in the coalescer/decanter, diluting the hydrochloric acid and adding LiCl did not affect the stability of the emulsion, but merely reduced the solubility of the methanesulfonyl chloride in the aqueous medium.

The present invention may be embodied in other specific forms without departing from the spirit or essential attributes thereof and, accordingly, reference should be made to the appended claims, rather than to the foregoing specification as indicating the scope of the invention.

I claim:

1. A process for separating an emulsion of alkanesulfonyl chloride in aqueous hydrochloric acid comprising passing the emulsion through a layer of alkanesulfonyl chloride; and allowing the emulsion to enter a settling vessel.

2. A process for separating an emulsion of alkanesulfonyl chloride in aqueous hydrochloric acid as in claim 1 further comprising passing the emulsion through a carbon bed.

3. A process according to claim 2 in which the carbon bed comprises carbon chips.

4. A process for separating an emulsion of alkanesulfonyl chloride in aqueous hydrochloric acid as in claim 2 wherein the carbon bed comprises graphite.

5. A process according to claim 4 in which the graphite comprises graphite chips.

6. A process according to claim 1 wherein the alkanesulfonyl chloride as 1-5 carbons.

* * * * *